US008741856B2

(12) United States Patent
Milani De Mayo De Mari et al.

(10) Patent No.: US 8,741,856 B2
(45) Date of Patent: Jun. 3, 2014

(54) AVERMECTINS AND MILBEMYCINS FOR THE TREATMENT, PREVENTION OR AMELIORATION OF FLAVIVIRUS INFECTIONS

(75) Inventors: Mario Milani De Mayo De Mari, Milan (IT); Eloise Mastrangelo, Milan (IT); Martino Bolognesi, Torre D'Isola (IT); Xavier De Lamballerie, Ensues La Redonne (FR); Boris Pastorino, Marseilles (FR); Johan Neyts, Kessel-Lo (BE); Suzanne Kaptein, Maastricht (NL)

(73) Assignees: Consiglio Nazionale Delle Ricerche, Roma (IT); Aix-Marseille Universite', Marseille (FR); Katholieke Universiteit Leuven-K.U. Leuven R&D, Leuven (BE)

( * ) Notice: Subject to any disclaimer, the term of this patent is extended or adjusted under 35 U.S.C. 154(b) by 41 days.

(21) Appl. No.: 13/503,660

(22) PCT Filed: Oct. 21, 2010

(86) PCT No.: PCT/EP2010/065880
§ 371 (c)(1),
(2), (4) Date: Apr. 24, 2012

(87) PCT Pub. No.: WO2011/051159
PCT Pub. Date: May 5, 2011

(65) Prior Publication Data
US 2012/0208778 A1    Aug. 16, 2012

(30) Foreign Application Priority Data
Oct. 28, 2009   (EP) .................................... 09174368

(51) Int. Cl.
*A61K 31/70*    (2006.01)

(52) U.S. Cl.
USPC ........................................................ 514/30

(58) Field of Classification Search
USPC ........................................................ 514/30
See application file for complete search history.

(56) References Cited

U.S. PATENT DOCUMENTS 4,199,569 A    4/1980   Chabala et al.

FOREIGN PATENT DOCUMENTS

| EP | 0170006 A2 | 2/1986 |
| EP | 0254583 A2 | 1/1988 |
| EP | 0334484 A2 | 9/1989 |
| EP | 0410615 A1 | 1/1991 |
| GB | 1390336 A | 4/1975 |
| GB | 1573955 A | 8/1980 |
| WO | 2009032975 A1 | 3/2009 |

OTHER PUBLICATIONS

Luigi De Colibus, Silvia Speroni, Bruno Coutard, Naomi L. Forrester, Ernest, Gould, Bruno Canard and Andrea Mattevi, Purification and Crystallization of Kokobera virus helicase, Acta Crystallographica section F, Structural Biology and Crystallization Communications, 2007, International Union of Crystallography, vol. 63, pp. 193-195, DOI: 1.1107/S1744309107005283.

CA Guzzo, CI Furtek, AG Porras, C Chen, R Tipping, CM Clineschmidt, DG Sciberras, JY Hsieh and KC Lesseter, Safety, tolerability, and pharmacokinetics of escalating high doses of ivermectin in healthy adult subject, The Journal of Clinical Pharmacology, 2002, vol. 42, pp. 1122-1133, The American College of Clinical Pharmacology.

Eloise Mastrangelo, Michela Bollati, Mario Milani, Nedege Brisbarre, Xavier De Lamballerie, Bruno Coutard, Bruno Canard, Alexander Khromykh and Martino Bolognesi, Preliminary crystallograpahic characterization of RNA helicase from Kunjin virs, Acta Crystallographica Section F, Structural Biololgy and Crystallization Communicationsc, 2006, International Union of Crystallography, vol. F62, pp. 876-879, DOI: 10:1107/S1744309106028776.

Eloise Mastrangelo, Mario Milani, Michela Bollati, Barbara Selisko, Frederic Peyrane, Vittorio Pandini, Graziella Sorrentino, Bruno Canard, Peter V. Konarev, Dmitri I. Svergun, Xavier De Lamballerie, Bruno Coutard, Alexander A. Khromykh and Martino Bolognesi, Crystal Structure and Activity of Kunjin Virus NS3 Helicase; Protease and Helicase Domain Assembly in the Full Length NS3 Protein, Journal of Molecular Biology, 2007, vol. 372, pp. 444-455, Elsevier Limited, DOI: 10.1016/J.

Jinhua Wu, Aloke Kimar Bera, Richard J. Kuhn, and Janet L. Smith, Structure of the Flavivirus Helicase: Implications for Catalytic Activity, Protein Interactions, and Proteolytic Processing, Journal of Virology, 2005, vol. 79, No. 16, pp. 10268-10277, American Solciety of Microbiololgy.

Alekseev A N, Chunikhin S P, Stefutkina L F, A trial at using the systemic action of ivermectin for suppressing the vector capacity of ticks (Ixodidae) infected with the tick-borne encephalitis virus, US National Library of Medicine, 1992, pp. 38-44.

*Primary Examiner* — Elli Peselev
(74) *Attorney, Agent, or Firm* — Robert E. Alderson, Jr.

(57) ABSTRACT

Avermectin and milbemycin compounds, particularly the substance ivermectin, for preparing an antiviral medicament for the treatment, prevention or amelioration of a *Flavivirus* infection, such as those caused by YFV (yellow fever virus), DENV (Dengue virus), JEV (Japanese encephalitis virus), TBEV (tick-borne encephalitis virus) or MODV (Modoc virus) are provided. The antiviral compositions of the present invention are suitable for oral administration to a *Flavivirus*-infected subject or a subject at risk of a infection, such as a human or other mammal.

7 Claims, 6 Drawing Sheets

EC50 JEV = 0.3 µM

B

EC50 TBEV = 0.2 µM

Figure 7

SEQUENCE LISTING

<160> NUMBER OF SEQ ID NOS: 2

<210> SEQ ID NO 1
<211> LENGTH: 30
<212> TYPE: RNA
<213> ORGANISM: artificial
<220> FEATURE:
<223> OTHER INFORMATION: PRIMER 1

<400> SEQUENCE: 1

```
caccucucua gagucgaccu gcaggcaucg                              30

<210> SEQ ID NO 2
<211> LENGTH: 16
<212> TYPE: RNA
<213> ORGANISM: artificial
<220> FEATURE:
<223> OTHER INFORMATION: PRIMER 2

<400> SEQUENCE: 2
cgacucuaga gaggug                                             16
```

AVERMECTINS AND MILBEMYCINS FOR THE TREATMENT, PREVENTION OR AMELIORATION OF FLAVIVIRUS INFECTIONS

CROSS-REFERENCE TO RELATED APPLICATIONS

This application is a National Phase Application of PCT International Application No. PCT/EP2010/065880, International Filing Date, 21 Oct. 2010, claiming priority to European Patent Application No. 09174368.2, filed 28 Oct. 2009, both of which are hereby incorporated by reference in their entirety.

FIELD OF THE INVENTION

The present invention relates to a novel therapeutic application of avermectins and milbemycins.

BACKGROUND OF THE INVENTION

The avermectins are a series of eight macrocyclic lactones ("macrolides") having a broad spectrum antiparasitic activity. These compounds, also designated as the "C-076 complex", are produced by the soil microorganism *Streptomyces avermitilis*. The isolation and chemical structure of the eight individual components of the C-076 complex is disclosed e.g. in GB 1573955, which is herein incorporated by reference. Selective hydrogenation products of the C-076 compounds and derivatives thereof are disclosed in U.S. Pat. No. 4,199,569.

The milbemycins are a group of antiparasite macrolides structurally related to the C-076 complex, distinguished from the avermectins in that they lack the sugar residue attached at the C-13 position. Examples of such compounds are disclosed e.g. in GB 1390336, EP 170006, EP 254583, EP 334484 and EP 410615.

Ivermectin falls within the group of avermectins. This substance consists of a mixture of 80% or more of avermectin $B_{1a}$ and 20% or less of avermectin $B_{1b}$. The structural formula of avermectin $B_{1a}$ and avermectin $B_{1b}$, is illustrated below:

Avermectin $B_{1a}$: R=$C_2H_5$; Avermectin $B_{1b}$: R=$CH_3$.

Ivermectin is a semi synthetic, anti-helmintic agent suitable for oral administration. In the mid 1980's, this active ingredient was introduced on the market as probably the broadest-spectrum anti-parasite medication ever. Traditionally it was used against worms (except tapeworms), but more recently it has been found to be effective against most mites and some lice as well. It is sold under the trademark names Stromectol in the United States, Mectizan in Canada by Merck, and Ivexterm in Mexico by Valeant Pharmaceuticals International. Mectizan is currently used to help eliminate river blindness (onchocerciasis) and stop transmission of lymphatic filariasis. Ivermectin kills the parasite by interfering with the nervous system and muscle function, in particular by enhancing inhibitory neurotransmission. The drug binds and activates glutamate-gated chloride channels (GluCls) present in neurons and myocytes. The main concern in connection with the administration of ivermectin is its neurotoxicity, which in most mammalian species can give rise to CNS depression and ataxia, as might be expected from potentiating inhibitory GABA-ergic synapses. Ivermectin is mainly used in humans in the treatment of onchocerciasis, but it is also effective against other worm infestations, such as strongyloidiasis, ascariasis, trichuriasis and enterobiasis. More recent evidence supports its off-label use in the treatment of mites such as scabies, usually limited to cases that prove resistant to topical treatments and/or which are in an advanced state, such as Norwegian scabies.

The present inventors have now surprisingly found that ivermectin is capable of inhibiting the enzymatic activity of *Flavivirus* helicase, an enzyme required for the replication of Flaviviruses.

DETAIL DESCRIPTION

Flaviviruses are a genus of ssRNA positive-strand viruses belonging to the Flaviviridae family. Most Flaviviruses are arthropod-borne viruses (Arboviruses), transmitted either by ticks (tick borne viruses, TBV) or by mosquitoes (mosquito borne viruses, MBV), but a number of Flaviviruses have no known vector (NKV) and/or have been isolated from infected animals without a known relation to a specific disease.

The genus *Flavivirus* consists of a number of different species. A list of the currently known *Flavivirus* species, downloaded from the NCBI Taxonomy Browser (http://www.ncbi.nml.nih.gov/Taxonomy/Browser), is provided herein below by way of illustration:

Aroa virus
    Bussuquara virus
    Iguape virus
    Naranjal virus
Dengue virus group
    Dengue virus
        Dengue virus 1
        Dengue virus 2
        Dengue virus 3
        Dengue virus 4
Japanese encephalitis virus group
    Japanese encephalitis virus
        Japanese encephalitis virus strain JAOARS982
        Japanese encephalitis virus strain Nakayama
        Japanese encephalitis virus strain SA(V)
        Japanese encephalitis virus strain SA-14
    Koutango virus
    Murray Valley encephalitis virus
        Alfuy virus
        Murray valley encephalitis virus (strain MVE-1-51)
    St. Louis encephalitis virus
        St. Louis encephalitis virus (strain MS1-7)
    Usutu virus
    West Nile virus
        Kunjin virus
        West Nile virus crow/New York/3356/2000
        West Nile virus H442
        West Nile virus SA381/00
        West Nile virus SA93/01
        West Nile virus SPU116/89
        West Nile virus strain 385-99
        West Nile virus strain PT5.2
        West Nile virus strain PT6.16
        West Nile virus strain PT6.39
        West Nile virus strain PT6.5
        West Nile virus strain PTRoxo
Kokobera virus group
    Kokobera virus
        New Mapoon virus
        Stratford virus
    unclassified Kokobera virus group
        CY1014 virus
Modoc virus group
    Cowbone Ridge virus
    Jutiapa virus
    Modoc virus
    Sal Vieja virus
    San Perlita virus
mosquito-borne viruses
    Ilheus virus
        Rocio virus
    Sepik virus
Ntaya virus group
    Bagaza virus
    Israel turkey meningoencephalomyelitis virus
    Ntaya virus
    Tembusu virus
        Sitiawan virus
    Yokose virus
Rio Bravo virus group
    Apoi virus
    Bukalasa bat virus
    Carey Island virus
    Dakar bat virus
    Entebbe bat virus
    Rio Bravo virus
    Saboya virus
        Potiskum virus
Seaborne tick-borne virus group
    Mcaban virus
    Saumarez Reef virus
    Tyuleniy virus
Spondweni virus group
    Zika virus
        Spondweni virus
tick-borne encephalitis virus group
    Kyasanur forest disease virus
        Alkhurma hemorrhagic fever virus
    Langat virus
        Langat virus (strain TP21)
        Langat virus (strain Yelantsev)
    Louping ill virus
        Louping ill virus (strain 31)
        Louping ill virus (strain K)
        Louping ill virus (strain Negishi 3248/49/P10)
        Louping ill virus (strain Norway)
        Louping ill virus (strain SB 526)
    Omsk hemorrhagic fever virus
    Phnom Penh bat virus
    Powassan virus
        Deer tick virus
        Tick-borne powassan virus (strain 1b)
    Royal Farm virus
        Karshi virus
    Tick-borne encephalitis virus
        Kumlinge virus
        Negishi virus
        Tick-borne encephalitis virus (strain HYPR)
        Tick-borne encephalitis virus (STRAIN SOFJIN)
        Tick-borne encephalitis virus (WESTERN SUBTYPE)
    Turkish sheep encephalitis virus
Yaounde virus
Yellow fever virus group
    Banzi virus
    Bouboui virus
    Edge Hill virus
    Uganda S virus
    Wesselsbron virus
    Yellow fever virus
        Yellow fever virus 17D
        Yellow fever virus 1899/81
        Yellow fever virus isolate Angola/14FA/1971
        Yellow fever virus isolate Ethiopia/Couma/1961
        Yellow fever virus isolate Ivory Coast/1999
        Yellow fever virus isolate Ivory Coast/85-82H/1982
        Yellow fever virus isolate Uganda/A7094A4/1948
        Yellow fever virus strain French neurotropic vaccine
        Yellow fever virus strain Ghana/Asibi/1927
        Yellow fever virus Trinidad/79A/1979
unclassified *Flavivirus*
    Aedes *flavivirus*
    Batu Cave virus
    Cacipacore virus
    Cell fusing agent virus
    Chaoyang virus
    Chimeric Tick-borne encephalitis virus/Dengue virus 4
    Culex *flavivirus*
    *Flavivirus* CbaAr4001
    *Flavivirus* FSME
    *Flavivirus* SST-2008

Gadgets Gully virus
Greek goat encephalitis virus
Jugra virus
Kadam virus
Kamiti River virus
Kedougou virus
Montana myotis leukoencephalitis virus
Ngoye virus
Nounane virus
Quang Binh virus
Russian Spring-Summer encephalitis virus
Sokoluk virus
Spanish sheep encephalitis virus
T'Ho virus
Tai forest virus B31
Tamana bat virus
Tick-borne *flavivirus*
Wang Thong virus
*Flavivirus* sp.

One of the most prominent members of the genus *Flavivirus* is the Yellow Fever Virus (YFV). This was the first human pathogenic virus isolated in 1927. Although a safe and efficient vaccine was produced in 1937, there are still more than 200,000 annual cases in Africa alone, and about 15% of the cases enter a critical phase with a chance of survival of about 50%.

In more recent years, the *Flavivirus* genus gained further attention due to the increasing incidence of infections caused by the West Nile Virus (WNV) in America, and the Dengue Virus (DENV) in subtropical areas of the world. WNV, isolated in Uganda in 1937, is endemic in Africa and Southern Europe, but its appearance in America in 1999 was followed by a rapid geographic spread from Canada to Argentina in 2008, resulting in thousands of deaths and disabled patients. Similarly, the four DENV serotypes have considerably spread all over the world in recent years. With billions of persons at risk, more than 50 million cases and about 12,500-25,000 deaths per year, DENV is robustly emerging in a growing number of countries.

Additional clinically significant Flaviviruses are the Japanese Encephalitis Virus (JEV) and the Tick-Borne Encephalitis Virus (TBEV). Japanese encephalitis (JE) is the leading cause of viral encephalitis in Asia, with 30,000-50,000 cases reported annually. Case-fatality rates range from 0.3% to 60%, depending on the population and age. Rare outbreaks in the US territories in Western Pacific have occurred. Residents of rural areas in endemic locations are at highest risk, since this infection does not usually occur in urban areas. Countries which had major epidemics in the past, but which have controlled the disease primarily by vaccination, include China, Korea, Japan, Taiwan and Thailand. There is no specific treatment available for Japanese encephalitis.

Tick-borne encephalitis is a viral infection of the central nervous system affecting humans and many other mammals. Russia and Europe report between 10,000-12,000 human cases per year. There is no remedy for the disease, but the infection can be prevented by vaccination. In humans, the disease is lethal in approximately 1% of cases and leaves 10-20% of its survivors with permanent neurological damages.

The Murine Favivirus Modoc (MODV) was first isolated in 1958 from white-footed deer mice in Modoc County, California. This virus was subsequently recognized as a *Flavivirus* and phylogenetic analysis placed MODV in the classical NKV group. MODV is neuroinvasive with a pathology similar to flaviviral encephalitis in humans.

There are a number of environmental, demographic and ecological reasons to believe that either novel or known Flaviviruses will keep emerging. In this respect, the shining success of vaccination against YFV has been hampered by difficulties encountered when such programs were launched against DENV. In particular, the presence of four DENV serotypes has complicated vaccine design because incomplete protection against one serotype may influence the disease outcome once infection is established by a different serotype, through a process known as "antibody-mediated disease enhancement". Therefore, in addition to vaccine design efforts, there has been a growing interest in the discovery of antiviral drugs effective against Flaviviruses.

The optimal *Flavivirus* drug should preferably be active against all the four DENV serotypes and some other Flaviviruses, such as e.g. YFV, WNV, TBEV and JEV. Additionally, it should be suitable for oral administration and should possess high oral bioavailability.

Ribavirin (1-beta-D-ribofuranosyl-1,2,4-triazole-3-carboxamide) is a broad-spectrum RNA virus replication inhibitor which, in combination with pegylated interferon, has proven to be effective against HCV infections. In an aerosol form, it is used for the treatment of paediatric respiratory syncytial virus (RSV) infections. Almost all of the RNA viruses as well as some DNA viruses are sensitive to the in vitro antiviral activity of ribavirin. However, Flaviviruses are much less sensitive to ribavirin than RSV. The effect of ribavirin was studied in rhesus monkeys infected with YFV or DENV type 1. Both therapeutic and prophylactic protocols were studied. However, no effect on viremia or survival was observed. Since the antiviral activity of ribavirin is based on a non-specific mechanism, the design of safe and more potent analogues of ribavirin is likely to be very difficult to achieve. EICAR, the 5-ethynyl analogue of ribavirin, was shown to be in vitro roughly 10- to 20-fold more potent in inhibiting *Flavivirus* replication. Such improved activity, however, corresponded to an increase in toxicity, which is explained by the fact that EICAR 5'-monophosphate is also more potent in inhibiting the IMP dehydrogenase.

Recently, a heterocyclic molecule with an in vitro anti-DENV activity was reported. Its mechanism of action is thought to be related to the inhibition of cellular IMP dehydrogenase.

In the light of the foregoing, a need still exists for an effective and specific anti-*Flavivirus* agent having reduced or no toxicity.

These and other needs are achieved by the present invention, which is based on the aforementioned finding that compounds belonging to the classes of avermectins and milbemycins, particularly the substance known as ivermectin, are capable of effectively inhibiting *Flavivirus* helicase, a viral enzyme required for the replication of Flaviviruses.

The present inventors have experimentally shown that ivermectin is specifically active against a number of viruses belonging to the genus *Flavivirus*, with an $EC_{50}$ in the nM range, which is indicative of good antiviral activity. In particular, such $EC_{50}$ value indicates that the active ingredient is effective at a concentration range in which ivermectin displays low toxicity and can therefore be safely used in animals and human beings, especially in view of previous studies suggesting that the molecule can be safely employed at doses up to 10 times the highest FDA-approved dose of 200 μg/kg (Guzzo C A et al. J. Clin. Pharmacol. 2002; 42:1122-33).

The inventors have further analyzed the effects of ivermectin on Flaviviruses in cell cultures, demonstrating that this drug is capable of dramatically inhibiting the replication of a number of clinically important Flaviviruses, such as the DENV, the JEV, the TBEV, for which no vaccine or effective inhibitor exists, as well as the YFV and the MODV.

The results obtained in a virus yield assay to assess viral RNA decrease by quantitative RT-PCR following ivermectin treatment, show that the $EC_{50}$ of ivermectin is in the nanomolar range for DENV, JEV, TBEV, YFV and MODV.

Based on the structural similarity shared by the antiparasite macrolides belonging to the classes of avermectins and milbemycins, said helicase-inhibiting activity is envisaged to be highly conserved within such classes.

Thus, an aspect of the present invention is a substance selected from the group of avermectins and milbemycins as defined in the appended claims for use in the therapeutic treatment of a *Flavivirus* infection, as well as the use of a substance as defined above for preparing an antiviral medicament for the therapeutic treatment of a *Flavivirus* infection.

Prominent representatives of such classes of substances include, without limitation, ivermectin, avermectin, doramectin, selamectin, moxidectin, emamectin, eprinomectin, milbemectin, abamectin, milbemycin oxime, nemadection and derivatives thereof, in a free form or in the form of a physiologically acceptable salt.

In a preferred embodiment of the invention, the substance is ivermectin. This drug is available on the market e.g. from Sigma Aldrich. Commercially-available ivermectin is a mixture of at least 80% avermectin $B_{1a}$ and 20% or less of avermectin $B_{1b}$.

Thus, according to a more preferred embodiment of the invention, the substance is a mixture of avermectin $B_{1a}$ in an amount of 80% or more and avermectin $B_{1b}$ in an amount of 20% or less. Even more preferably, the substance is avermectin $B_{1a}$.

The use of ivermectin as a medicament in the present invention is particularly preferred in view of its effective inhibiting activity against the replication of a number of different *Flavivirus* species, and also in view of the fact that this drug is currently available on the market as a medicament authorized for oral administration. Thus, obtaining a marketing authorization for ivermectin as an antiviral medicament for oral administration will probably not require to perform phase 1 and phase 2 trials.

Furthermore, the inventors have found that ivermectin is specifically effective against the genus *Flavivirus*. As a matter of fact, no antiviral activity was observed either against other Flaviviridae viruses or against other virus families.

In view of the experimental studies carried out by the present inventors including, inter alia, the determination of the $EC_{50}$ value as mentioned above, the antiviral medicament against *Flavivirus* infections is preferably provided as an oral pharmaceutical dosage form. Non limiting examples of pharmaceutical dosage forms suitable for oral administration are a pill, a tablet, a capsule, a liquid solution or suspension, a powder.

By way of example, a dose suitable for oral administration to a subject in need of an anti-Flaviviral treatment is comprised between about 50 to about 2000 μg/kg of body weight. Such a dose may be provided as a single administration or it can be divided in a plurality of administrations, e.g. 2 or 3 administrations.

Within the scope of the present description, the subject to be administered with avermectin or milbemycin according to the present invention is a mammal This expression is intended to encompass any mammal, including inter alia a human being.

The following is a detailed description of the tests and studies carried out by the present inventors in order to demonstrate and characterize the antiviral activity of ivermectin.

The following detailed description is provided by way of illustration only, with reference to the appended drawings wherein:

BRIEF DESCRIPTION OF THE DRAWINGS

FIG. 6 shows the results of the virus yield assay carried out to assess the anti-MODV activity of ivermectin.

FIG. 7 shows the results of the virus titration assay carried out to assess A) the Anti-JEV and B) the anti-TBEV activity of ivermectin.

The target-based design of inhibitors of flaviviral enzymes may be a promising strategy towards the development of selective inhibitors of *Flavivirus* replication.

The *Flavivirus* genome encodes a 370 kDa polyprotein precursor that is partly inserted into the membrane of the endoplasmic reticulum. Subsequently, the polyprotein is processed by cellular and viral proteases to yield three mature structural proteins (designated as C, M, and E, respectively), and seven non-structural proteins (designated as NS1, NS2A, NS2B, NS3, NS4A, NS4B and NS5, respectively). During replication, the viral genome is transcribed into a negative-strand RNA and used as template to synthesise the daughter viral genomic RNA. Many viral proteins are required for RNA replication. Some of the non-structural proteins are multi domain proteins endowed with more than one function. Besides the evident role of the RdRp (RNA-dependent RNA polymerase, the C-terminal domain of NS5) to maintain proper viral replication, the nascent transcript must be unwound from its complementary template RNA. This is performed by the C-terminal domain of NS3 (the "helicase domain"). Then, the newly synthesized RNA must be properly capped (cap I structure) and this process requires three enzyme activities: a RNA triphosphatase activity (the C-terminal domain of NS3), a guanylyltransferase activity (likely the N-terminal domain of NS5) and a methyltransferase activity (MTase; the N-terminal domain of NS5). Therefore, NS3 (N-terminal protease and C-terminal helicase activity) and NS5 (N-terminal MTase and C-terminal RdRp) are the main actors of the viral replication in the context of a multiprotein complex, likely comprising proteins from the host cell too.

The inventors selected the C-terminal NS3 helicase domain of the genus *Flavivirus* as a valuable drug target. Compounds based on the structure of nucleoside-5'-triphosphates are an attractive tool for inhibition of the helicase activity. However, it is known that analogues of nucleoside-5'-triphosphates, with a modified base such as ribavirin-TP, IDA-TP or ITA-TP, when tested at ATP concentrations equal to the $K_m$, values determined for the ATPase reaction of each of the viral enzymes, inhibit only weakly the ATPase reaction mediated by NTPase/helicases from HCV, JEV, DENV and WNV. Moreover, since many distinct mammalian metabolic enzymes require ATP as an energy source, an ATP-mimetic compound may turn out to be generally toxic.

Figure 1:
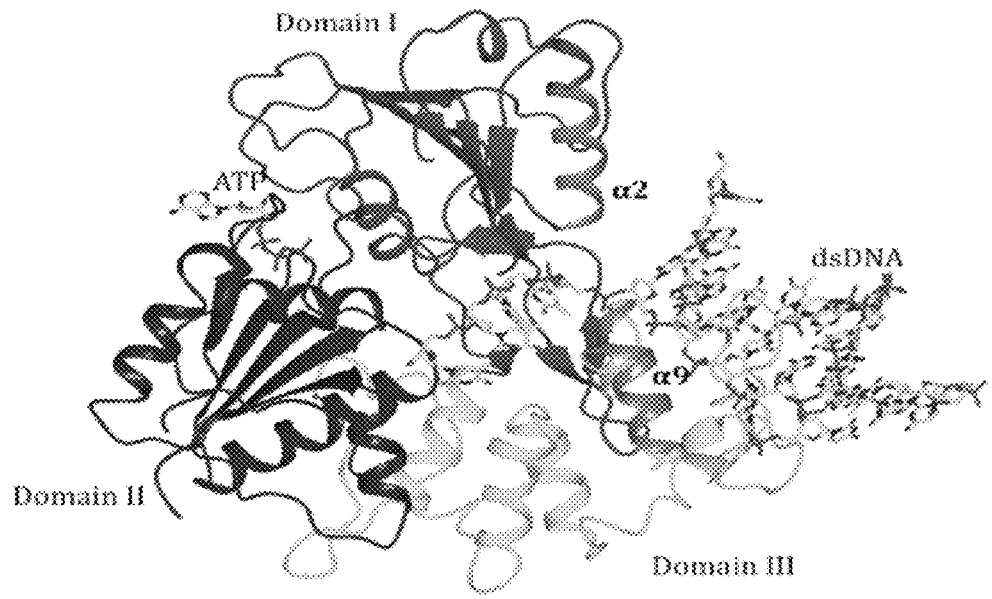
FIG. 1 is a schematic representation of the crystal structure of the Kunjin virus NS3 helicase domain (Protein Data Bank entry 2QEQ; Mastrangelo E et al. J. Mol. Biol. (2007) 372, 444-455). Domains I (in gray) and II (in black) are structurally similar, each of them being composed of six β-strands surrounded by four and three α-helices, respectively. Domain III (in light gray) is composed of five parallel α-helices and two antiparallel β-strands. The inventors modelled the position of a dsDNA (sticks) segment by superposition of KUNV NS3 residues 186-619 on the DNA-bound bacterial helicase PcrA (pdb: 3PJR). Helices α2, of domain II, and α9, of domain III, forming the opposite sides at the entry crevice, are recalled in the figure.

A different helicase inhibitor search strategy should therefore, in principle, be directed to the inhibition of the enzyme's RNA handling mechanisms. For the search of inhibitors based on such a new conceptual scheme, the inventors targeted the helicase ssRNA access site. An in silico model of the helicase/RNA interaction was produced and used to identify a likely ssRNA access site to the enzyme active region (FIG. 1). The selected region was then explored in silico using compounds from the public LOPAC library (Sigma-Aldrich) of available low molecular weight compounds.

Based on the results obtained from the in silico studies, ivermectin was selected, together with a number of other molecules, for subsequent in vitro helicase activity inhibitory tests. The inventors surprisingly found that, amongst the group of candidate helicase inhibitors identified by the in silico studies, only ivermectin shows the expected activity.

The helicase inhibitory activity of ivermectin was demonstrated by in vitro assays carried out on the helicase domains of two different Flaviviruses: the Kunjin virus and the Kokobera virus. The Kunjin virus and Kokobera virus helicase domain were expressed and purified as described (Mastrangelo et al., Acta Cryst. (2006). F62, 876-879; De Colibus et al., Acta Cryst. (2007). F63, 193-195). Example 1 in the experimental section below discloses the production of the recombinant helicase domains in Escherichia coli.

The helicase inhibition activity was assessed using a radio-labeled RNA substrate in the presence of $Mg^{2+}$ and ATP. The RNA substrate was prepared as described in Wu, J. et al. (2005) Structure of the *Flavivirus* helicase: implications for catalytic activity, protein interactions, and proteolytic processing. J. Virol. 79, 10268-10277. Example 2 discloses the helicase activity inhibition assays carried out on the helicase domains obtained according to Example 1.

Figure 3:
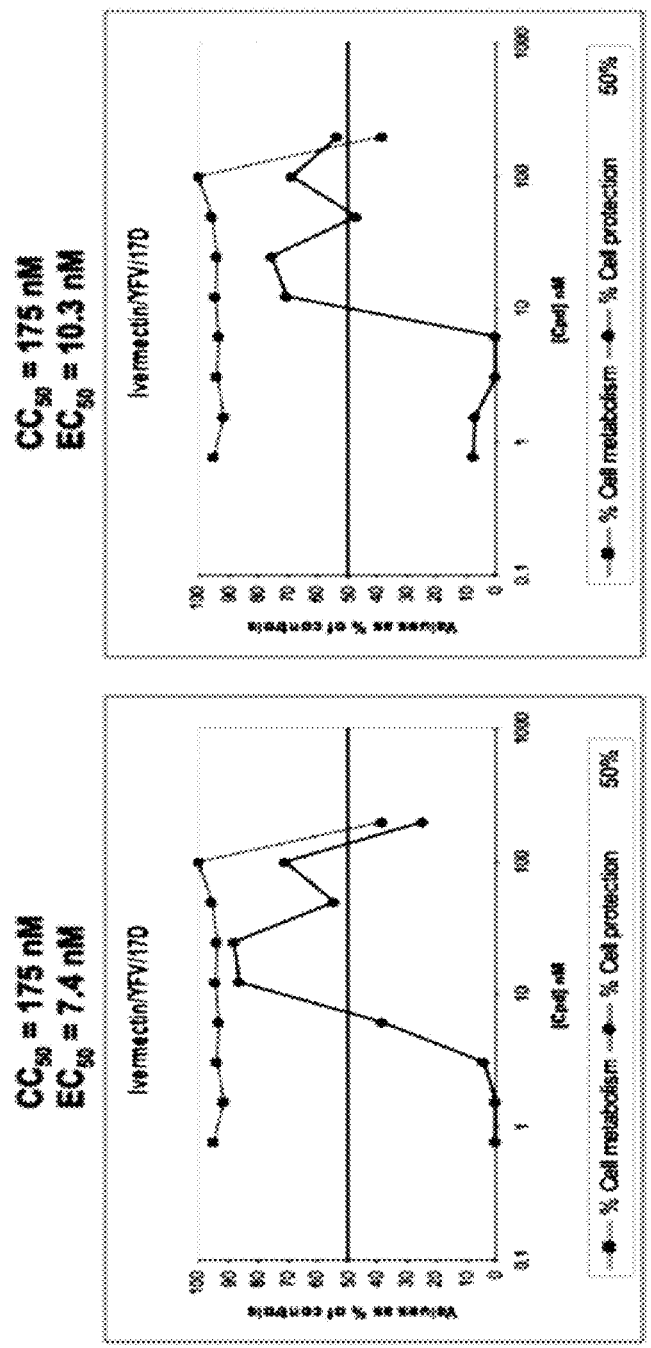
FIG. 3 shows the results of the CPE reduction assay used to assess the anti-YFV activity of ivermectin.

Inhibition assays performed on infected cells showed a potent antiviral activity of ivermectin against YFV, DENV, JEV, TBEV and MODV. In particular, ivermectin was shown to possess an anti-YFV activity by both a CPE reduction assay ($EC_{50}$=7.4 and 10.3 nM; FIG. 3) and a virus yield reduction assay (quantification by RT-PCR; $EC_{50}$=4.9 nM).

Figure 4:
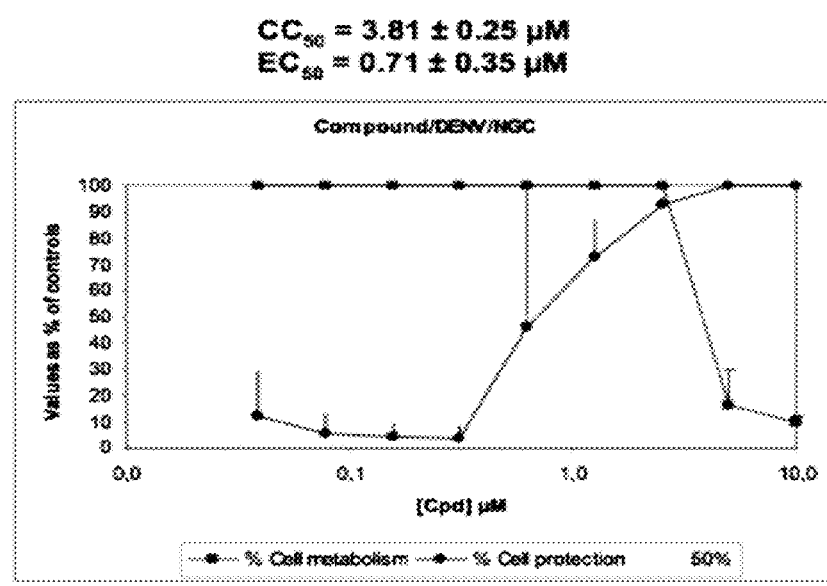
FIG. 4 shows the results of the virus yield assay used to assess the anti-DENV activity of ivermectin.
Figure 5:
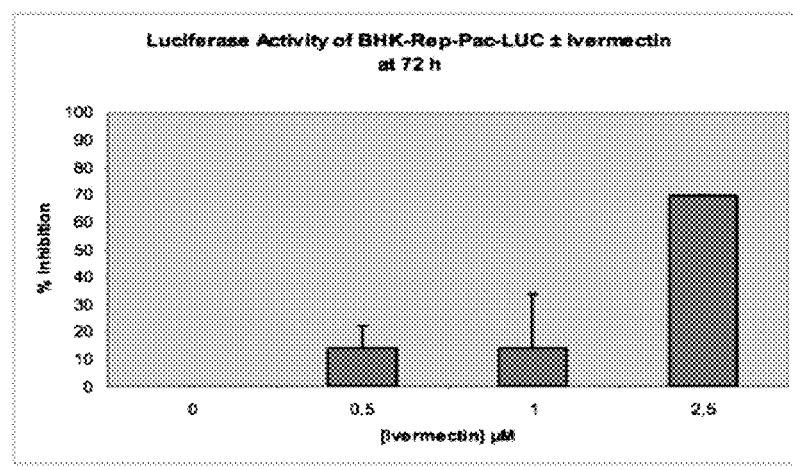
FIG. 5 shows the results of the assay carried out to assess the anti-DENV activity in BHK cells containing Dengue subgenomic replicons.

The anti-DENV activity ($EC_{50}$=710+/−350 nM) was demonstrated by a virus yield reduction assay (quantification by RT-PCR; FIG. 4). Ivermectin was also shown to possess anti-DENV activity in BHK cells containing Dengue subgenomic replicons (FIG. 5).

Figure 6:
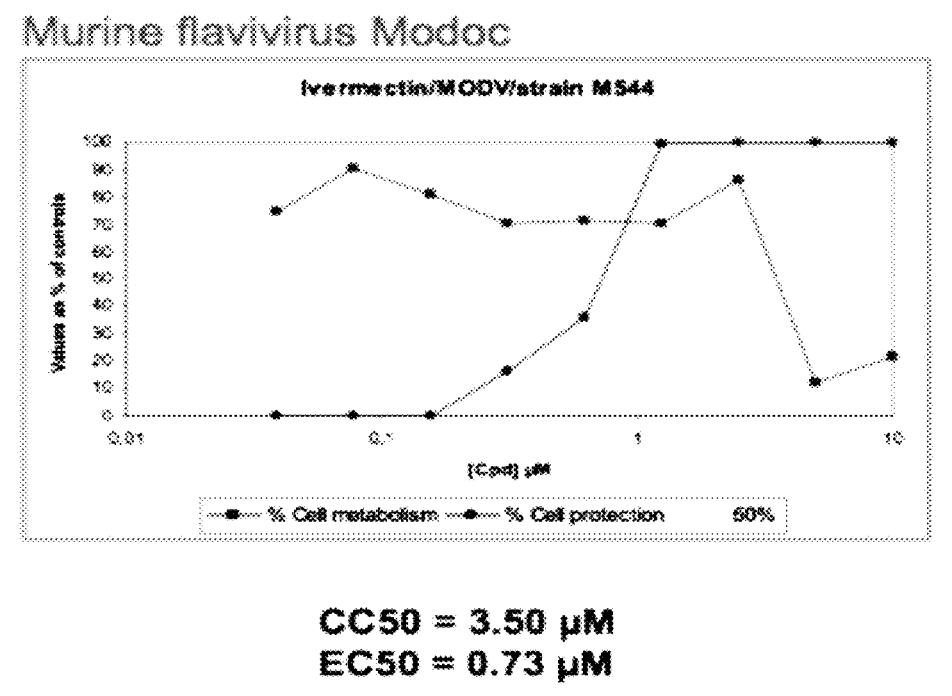

The effectiveness of ivermectin as an antiviral agent was also shown against the related *Flavivirus* MODV ($EC_{50}$=730 nM) by a virus yield reduction assay (quantification by RT-PCR) (FIG. 6).

Figure 7:
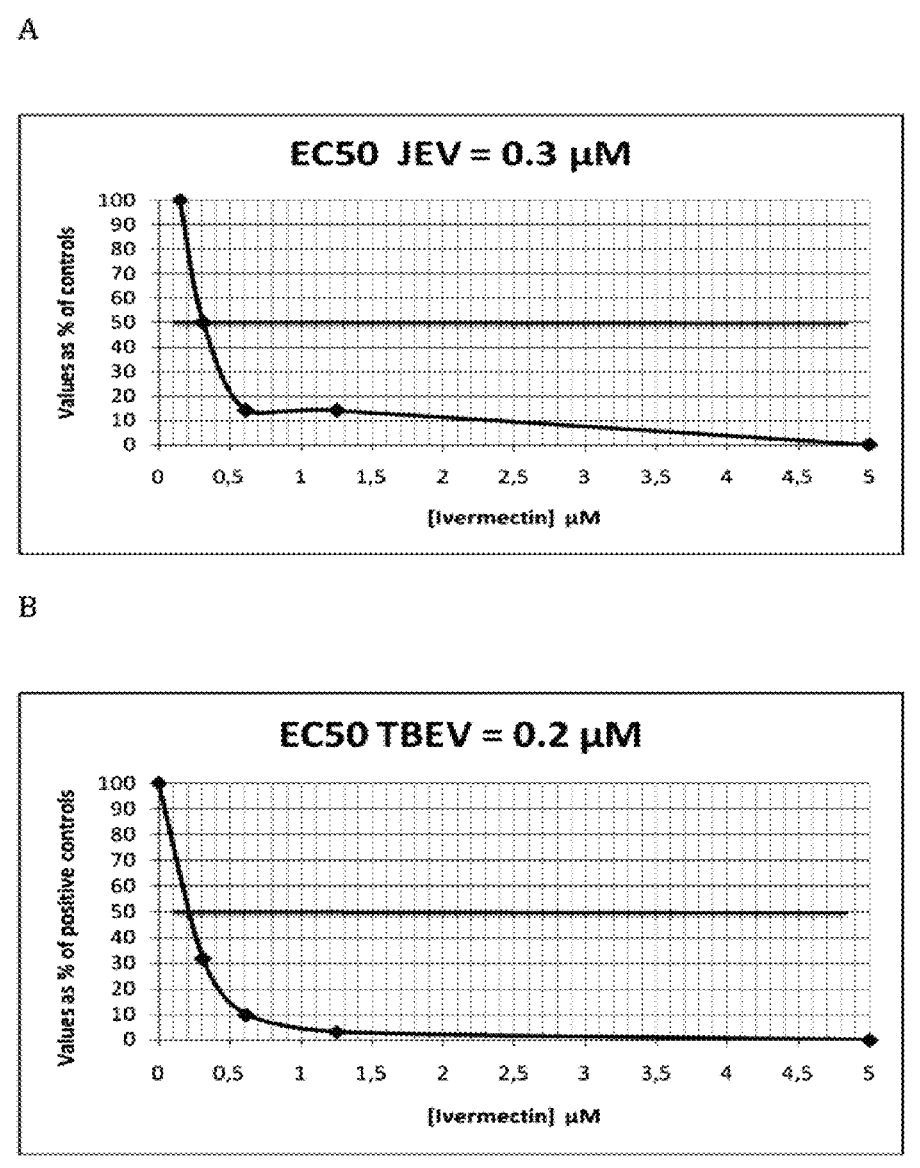

Furthermore, in a virus yield assay carried out with Vero cells seeded on a 24-wells plate, an MOI of about 0.1-1, analysis of the cell culture supernatant 72 hours post infection, quantification of the antiviral activity by quantitative RT-PCR, the ivermectin $EC_{50}$ values were of about 100-1000 nM for both JEV and TBEV. Part of each corresponding cell supernatant was removed and stored at −80° C. before viral titration on BHK21 cells (TCID50/ml). The viral titration on BHK21 cells showed that the ivermectin $EC_{50}$ values were 300 and 200 nM for JEV and TBEV, respectively (FIG. 7, A and B).

The selectivity of the antiviral activity of ivermectin against the genus *Flavivirus* was shown by its failure to inhibit Bovine viral diharrea virus (BVDV), which belongs to the genus Pestivirus of the family Flaviviridae. Effectively the ivermectin concentration required to achieve 50% protection of mock-infected MDBK (Bovine normal kidney) cells from the BVDV induced cytopathogenicity is about 1.5 µM as determined by the MTT method (ivermectin concentration required to reduce the viability of MDBK cells by 50% being 11 µM). Moreover ivermectin does not inhibit other viruses belonging to several other families such as Coxsackievirus B2 (CVB-2) and Poliovirus 1 (Sb-1; ss(+)RNA virus; Picornaviridae family); Herpesvirus 1 (HSV-1; dsDNA virus; Herpesviridae family) and Vaccinia Virus (VV; dsDNA virus; Poxviridae family); Vesicular Stomatitis Virus (VSV; ss(−) RNA virus; Rhabdoviridae family) and Respiratory Syncytial Virus (RSV; ss(−) RNA; Paramixoviridae family), for which the ivermectin concentration required to reduce the plaque number by 50% in mock-infected VERO-76 (Monkey normal kidney) monolayers is >6 µM (ivermectin concentration required to reduce the viability of VERO 76 monolayers by 50% being 6 µM). Furthermore in the Reoviridae family (ss(+)RNA virus) the ivermectin concentration required to achieve 50% protection of mock-infected BHK cells (Hamster normal kidney fibroblast) from the Reovirus-1 (Reo-1) induced cytopathogenicity, is >1.5 µM (ivermectin concentration required to reduce the viability of BHK monolayers by 50%, being 1.5 µM).

EXAMPLE 1

Production of the Complete Helicase Domains

Briefly, PCR products were obtained that include the complete helicase domains. They were re-amplified using GATE-WAY-modified designed to encode N-terminal $(His)_6$-tagged recombinant proteins spanning amino acids 186-620 of the Kunjin NS3 gene and 189-620 of the Kokobera NS3 gene. Each of these products were subsequently cloned into pDEST 14 HN expression vector and the Kunjin and Kokobera constructs were transformed respectively into *Escherichia coli* Rosetta (DE3) pRos and C41 (DE3) pRos strains and the cells were grown in SB at 17° C. and 2YT medium at 20° C. respectively.

After the induction with 0.5 mM isopropyl β-D-thiogalactopyranoside (IPTG), the cells were grown for 16 hours and harvested by centrifugation then lysed in the lysis buffer by sonication. After the centrifugation at 23.000 g for 1 h, the supernatants were loaded on a metal affinity HisTrap HP column; recombinant helicase domains, eluted at 250 mM imidazole, were subsequently loaded onto an HiLoad 16/60 Superdex 200 column. Kunjin virus helicase domain was eluted using NaCl 100 mM, DTT 1 mM, Bicine 10 mM pH 8.5, and concentrated to 4 mg $ml^{-1}$. Kokobera helicase domain was eluted using 10 mM imidazole, 300 mM NaCl pH 8.0 and concentrated to 14 mg $ml^{-1}$.

EXAMPLE 2

Helicase Activity Inhibition Assays

Figure 2:
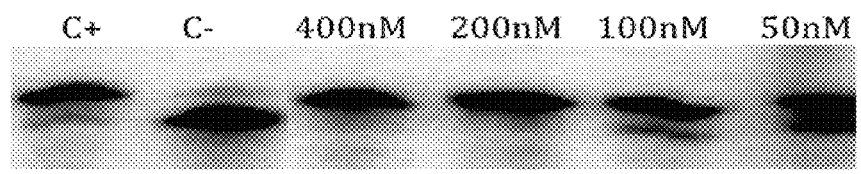
FIG. 2 shows the results of the in vitro inhibition assay carried out using Kokobera virus helicase domains. The two lanes on the left host the positive control (+Control) in the absence of enzyme and the negative control (−Control; heat-denatured duplex).

Briefly, primer 1 (5'-CACCUCUCUAGAGUCGACCUG-CAGGCAUCG-3', SEQ ID NO:1) was labelled at its 5' end with T4 polynucleotide kinase and [$\gamma$-$^{32}$P]ATP, and annealed with the complementary primer 2 (5'-CGACUCUAGAGAG-GUG-3', SEQ ID NO:2). The helicase domains (200 nM each) were pre-incubated with an amount of ivermectin (Sigma Aldrich, cat. no. 18898) comprised between 50 and 400 nM. The reactions were initiated by the addition of the proteins to the reaction mixture containing 6 fmol of RNA and were quenched after 30 min at 37° C. by the addition of 6 µl of loading dye (50 mM EDTA, 0.5% SDS, 50% glycerol, 0.1% Bromophenol Blue). The assay mixtures were subjected to electrophoresis on non-denaturing 17% polyacrylamide gels that were dried and analyzed by phosphoimage (Typhoon, GE-Healthcare). The gels showed that ivermectin is able to inhibit the activity of the two helicase domains at a concentration ranging between 50 and 100 nM (FIG. 2).

EXAMPLE 3

Antiviral Assay

To each well of a 96-well plate 100 µl of culture medium containing 100 CCID$_{50}$ (i.e. 50% cell culture infectious dose) of virus was added to each well after which two-fold serial dilutions of the compounds and 100 µl cell suspension (2.5× 10$^4$ Vero-B) was added. After a one-week incubation, culture medium was discarded and cell metabolic activity was quantified using the ATP-Lite method. The percentage cytopathic effect (CPE) was calculated as follows: % CPE=100× [(OD$_{Virus+Compound}$−OD$_{VC}$)/(OD$_{CC}$−OD$_{VC}$)]. In this formula, OD$_{CC}$ represents the optical density of the uninfected untreated cells, whereas OD$_{VC}$ and OD$_{Virus+Compound}$ represent the optical densities of infected, untreated cells and virus-infected cells that were treated with a given concentration of compound, respectively. The 50% effective concentration (EC$_{50}$), which is defined as the compound concentration that is required to inhibit virus-induced CPE by 50%, was determined using logarithmic interpolation. Ribavirin was included as a reference compound.

Viruses

Modoc (MODV) strain M544 [American Type Culture Collection (ATCC) VR415] was propagated in BHK-21 cells. Yellow fever virus (YFV) 17D vaccine strain (Stamaril) [Aventis Pasteur (MSD, Brussels, Belgium)] was passaged once in Vero-B cells to prepare a working virus stock and stored at −80° C. until further use. Dengue virus (DENV) serotype 2 New Guinea C (NGC) strain was cultivated in either Vero-B or C6/36 mosquito cells.

Cytotoxic and Cytostatic Assay in Vero-B Cells

Potential cytotoxic effects of the compounds were evaluated in uninfected quiescent Vero-B cells. The cells were seeded at $1\times10^4$ cells/well in a 96-well plate in the presence of two-fold serial dilutions and incubated for one week. After one week, the culture medium was discarded and 100 μl 3-(4,5-dimethylthiazol-2-yl)-5-(3-carboxymethoxyphenyl)-2-(4-sulfophenyl)-2H-tetrazolium/phenazinemethosulfate (MTS/PMS; Promega, Leiden, The Netherlands) in PBS were added to each well. Following a 2-hour incubation at 37° C., the optical density was determined at 498 nm. The cytotoxic activity was calculated using the following formula: % $CPE=100\times(OD_{Compound}/OD_{CC})$, where $OD_{Compound}$ and $OD_{CC}$ are the optical density at 498 nm of the uninfected cell cultures treated with the compound and of the uninfected, untreated cell cultures, respectively. The 50% cytotoxic concentration (i.e., the concentration that reduces the total cell number with 50%; $CC_{50}$) was calculated by linear interpolation.

The screening was performed onto Vero cells grown in 24-well tissue culture plates. The virus infection was obtained using either the JEV strain SA-14 (GenBank accession number U14163) and the TBEV strain Oshima 5-10 (GenBank accession number AB062063). Viral strains were used at a dilution of MOI<1, (i.e. between 0.1 and 1).

Ivermectin was used at a final concentration ranging between 0 and 10 μM. A pre-incubation in the presence of the antiviral was performed during the 90-minute virus adsorption step. Briefly, when Vero cells reached 90% confluence, the cell supernatant was removed and replaced by 100 μl of a medium mixture containing the virus and the antiviral compound at the targeted concentration (10, 5, 2.5, 1.25, 0.6, 0.3, 0.15 and 0 μM). After 1 h 30 at 37° C., the cells were washed once with 400 μl PBS. Subsequently, 1 ml of fresh complete medium plus antiviral compound at the targeted concentration (10, 5, 2.5, 1.25, 0.6, 0.3, 0.15 and 0 μM) was added in each wells and the plates were incubated for 72 h at 37° C., under 5% $CO_2$ until analysis. All conditions were assayed in duplicate. 72 hours-post-infection, each corresponding cell culture supernatant was removed, clarified by centrifugation and stored at −80° C. before analysis using a viral titer reduction assay.

The viral titer reduction assay was performed using BHK21 cells seeded in 96-well plates. When the cells reach 80% confluence, they were infected with 150 μl of ten-fold serial dilutions of the virus (targeted Vero cell clarified supernatants) for 4 days before microscopic examination and positive ECP well counting. For each supernatant sample, the infectivity titer was expressed as TCID50/ml using the Karber formulae. For each virus, titers of viral supernatants were then compared and represented as % of positive control (viral titer from infected cell supernatant sample without antiviral compound) for the calculation of $IC_{50}$ values.

The results provided by the viral titer reduction assay are as follows: $EC_{50}$=0.3 μM for JEV and $EC_{50}$=0.2 μM for TBEV (see FIG. 7). The results were secondarily confirmed using a virus yield reduction assay (quantification by RT-PCR, data not shown).

The invention claimed is:

1. A method for treating a Flavovirus infection in a patient, comprising:

administering to said patient a composition comprising a therapeutically effective amount of an avermectin or milbemycin compound selected from the group consisting of: ivermectin, doramectin, selamectin, moxidectin, emamectin, eprinomectin, milbemectin, abamectin, milbemycin oxime, nemadectin and macrolide derivatives thereof lacking a sugar residue at the C-13 position, alone or in combination, wherein the foregoing are in a free form or in the form of a physiologically acceptable salt.

2. The method of claim 1, wherein the *Flavivirus* is selected from the group consisting of YFV (yellow fever virus), DENV (Dengue virus), JEV (Japanese encephalitis virus), TBEV (tick-borne encephalitis virus) and MODV (Modoc virus).

3. The method of claim 1, wherein the composition comprises ivermectin.

4. The method of claim 1, wherein the composition comprises a combination of avermectin $B_{1a}$ in an amount of about 80% or more and avermectin $B_{1b}$ in an amount of about 20% or less.

5. The method of claim 1, wherein the composition comprises avermectin $B_{1a}$.

6. The method of claim 1, wherein the composition is in a form suitable for oral administration.

7. The method of claim 6, wherein the composition is in a form suitable for administering a dose of the compound between about 50 and about 2000 µg/kg of body weight, either in a single dose or in a plurality of divided doses.

* * * * *